(12) United States Patent
Banfield et al.

(10) Patent No.: US 8,808,721 B2
(45) Date of Patent: Aug. 19, 2014

(54) BED BUG ATTRACTANTS AND METHODS FOR TRAPPING BED BUGS

(75) Inventors: Michael Gilbert Banfield, Woodinville, WA (US); Elizabeth Joy Schaafsma, Seattle, WA (US)

(73) Assignee: SpringStar Inc., Woodinville, MA (US)

( * ) Notice: Subject to any disclaimer, the term of this patent is extended or adjusted under 35 U.S.C. 154(b) by 0 days.

(21) Appl. No.: 13/466,880

(22) Filed: May 8, 2012

(65) Prior Publication Data

US 2012/0285076 A1    Nov. 15, 2012

Related U.S. Application Data

(60) Provisional application No. 61/484,114, filed on May 9, 2011.

(51) Int. Cl.

| | |
|---|---|
| *A01N 25/32* | (2006.01) |
| *A01N 25/08* | (2006.01) |
| *A01N 37/02* | (2006.01) |
| *A01N 37/06* | (2006.01) |
| *A01N 43/38* | (2006.01) |
| *A01N 25/18* | (2006.01) |
| *A01M 1/02* | (2006.01) |
| *A01M 1/10* | (2006.01) |
| *A01M 1/14* | (2006.01) |
| *A01N 25/00* | (2006.01) |

(52) U.S. Cl.
CPC ............ *A01M 1/026* (2013.01); *A01N 25/18* (2013.01); *A01M 1/103* (2013.01); *A01M 1/14* (2013.01); *A01N 25/006* (2013.01)
USPC .............. 424/406; 43/123; 424/84; 424/178; 424/405; 424/409; 424/410; 424/412; 424/512; 424/513; 424/558; 424/613; 424/675; 424/700; 424/715

(58) Field of Classification Search
None
See application file for complete search history.

(56) References Cited

U.S. PATENT DOCUMENTS

| | | | | |
|---|---|---|---|---|
| 7,743,552 B2 * | 6/2010 | Borth et al. | ...................... | 43/131 |
| 8,404,260 B2 * | 3/2013 | Reid et al. | ...................... | 424/405 |

* cited by examiner

*Primary Examiner* — Neil Levy

(57) ABSTRACT

The present invention relates to compositions and methods for attracting bed bugs with novel attractants and new and improved methods to enable their use to attract, monitor or trap bed bugs for surveying, monitoring, mitigation and management purposes. Known mammal pheromones were discovered to be useful as bed bug kairomone attractants. A method of delivering non-volatile attractants by using the attractive heat source to heat and volatilize the attractants was discovered to be the optimal method to disseminate the kairomones. A new method of generating low levels of carbon dioxide is disclosed, and the combination of kairomones, carbon dioxide and heat is shown to attract bed bugs.

3 Claims, 6 Drawing Sheets

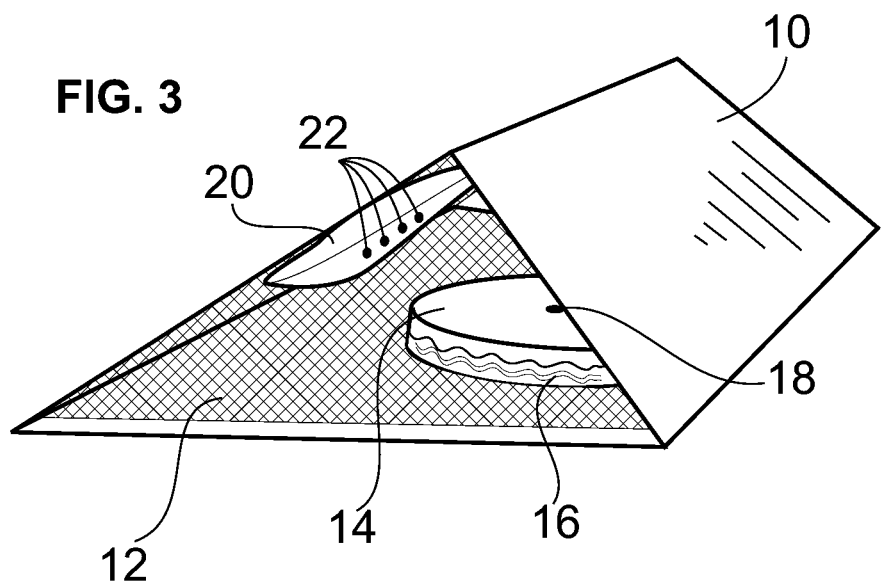
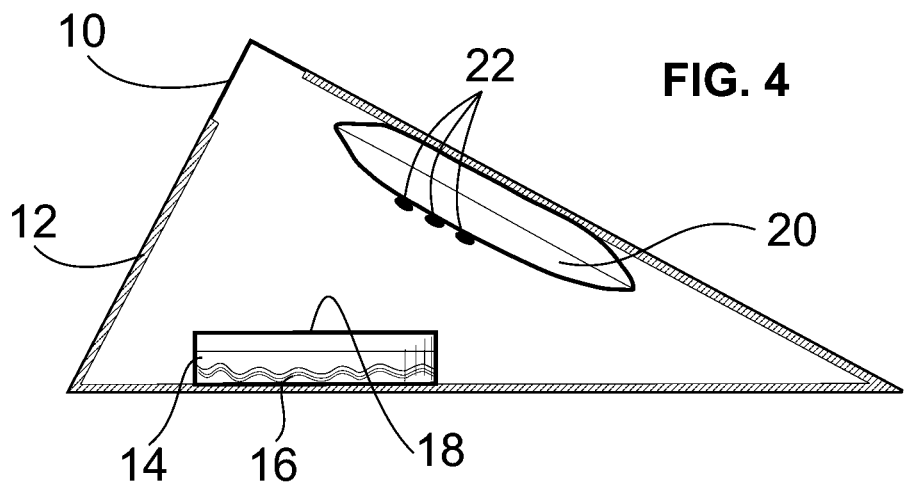

BED BUG ATTRACTANTS AND METHODS FOR TRAPPING BED BUGS

CROSS-REFERENCE TO RELATED APPLICATIONS

This application claims the benefit of U.S. Provisional Application Ser. No. 61/484,114 filed on 9 May 2011, which is incorporated in its entirety by this reference.

FIELD OF THE INVENTION

This invention relates to new and improved bed bug attractant compositions and new and improved methods to enable use of the attractant compositions to attract, monitor or trap bed bugs for surveying, monitoring, mitigation and management purposes.

BACKGROUND OF THE INVENTION

The common bed bug, Cimex lectularius and the related tropical bed bug Cimex hemipterus are cosmopolitan pests of human habitation, with documented infestations dating back to ancient Greece and Pharaonic Egypt. With the advent of DDT and other synthetic insecticides during WWII, bed bugs became a rarity in industrialized countries. As bed bugs are not known to transmit human disease, scientific interest in them waned along with their prevalence. Since the 1990s, however, many countries including the United States have experienced exponential increases in bed bug populations. This widespread resurgence is attributed to a combination of insecticide resistance, changes in control strategies for other urban pests, and an increase in travel both within and between countries. The problem is exacerbated by a reduction in the number available efficacious pesticides, either through product cancellations or regulatory restrictions.

Bed bugs are difficult to find and identify because of their small size and cryptic habits. Their bodies, which are 1-7 mm long and dorso-ventrally flattened, allow them to hide in narrow cracks. They are generally nocturnal, with maximum activity between midnight and 6:00 am. Under ideal laboratory conditions, bed bugs will go through five nymphal stages, each lasting 4-8 days before a final molt to an adult stage. Depending on the strain of bed bug, their level of resistance to pesticides, activity level, the ambient temperature and humidity, and host availability, adult bed bugs may live for anywhere from three months to four years.

A variety of techniques and devices may be used to monitor or trap bed bugs for surveying, monitoring, mitigation and management purposes. Visual inspections are commonly used to detect bed bugs, but are time and labor-intensive; even trained individuals can miss large numbers of insects. Bed bug-sniffing dogs are an increasingly common survey method, especially for detecting low-level infestations, but dogs are expensive to train and employ, are not available in all areas, and their accuracy can vary widely between dog-and-handler teams. Recent studies have demonstrated the potential for trapping as a viable alternative to visual or canine inspections in confirming the presence and size of an infestation (Wang et al. J. Econ. Entomol. 2010, 103:172-177).

Current bed bug mitigation devices range from unbaited, passive sticky traps of various designs, pitfall traps, heating units with either a sticky means or a pitfall means, carbon dioxide generators with either a sticky means or a pitfall means, and combinations that include insect-mediated compounds and/or host mediated compounds with a sticky means, pitfall means or a monitoring or other insect detection system. These devices are of limited utility as they can fail to mitigate bed bugs either in the presence or absence of a host. These traps are not able to efficiently attract, trap, and kill an adequate number of bed bugs, thus resulting in scenarios that necessitate additional efforts for surveying, monitoring, mitigation and management purposes.

Bed bug attractants fall into two discrete categories: insect-mediated compounds or host-mediated compounds. Insects use a set of compounds in their chemical ecology, which are commonly present in harborage areas and involve mating, aggregation, alarm or arresting pheromones (i.e. Siljander et al. U.S. Pat. No. 7,892,528). Primary host-mediated factors are carbon dioxide, and heat, and are involved in host location by bed bugs. Few effective host-produced chemicals have been discovered. Many such compounds have been hypothesized from the host cues used by mosquitoes and other blood-feeding insects, such as lactic acid and butyric acid.

The currently-accepted threshold of attraction for bed bugs using carbon-dioxide is a release rate of 50 milliliters (mL) per minute (Anderson et al. Med. Vet. Ent., 2009, 23:99-105). This rate necessitates that large quantities of compressed gas, dry ice, or acid/mineral mixture is required to generate a sufficient quantity of carbon-dioxide. This limits the portability, duration of release and size of attractant device available, and makes said devices expensive. It is known carbon dioxide can be generated by microbial means, but no method has been shown to attract bed bugs at a low release rate, over a period longer than 1 to 7 days. Thus, an improved method of generating carbon dioxide in quantities sufficient to attract bed bugs is desired.

In addition, there is a need for a method which includes both a short-term, low cost, disposable monitoring system, but which can also be economically used over a term longer than 10 days.

Thus, there is a need in the bed bug detection field to create new and improved bed bug attractant compositions and new and improved methods to enable their use to attract, monitor or trap bed bugs for surveying, monitoring, mitigation and management purposes. This invention provides such improvements.

BRIEF DESCRIPTION OF THE DRAWINGS

FIG. 3 schematically illustrates another trap (ST), suitable for short term use in the present invention. The trap is shown in an oblique view. The paper insect trap consists of a piece of 0.045 cm thick paper 10, 12.5 cm wide and 36.5 cm long, which has been folded into a triangular shape. The inside of the trap 10 is coated with a pressure-sensitive, non-drying adhesive 12. A handwarmer 20, which produces heat through iron oxidation reaction, is affixed to the upper inside face of the trap 10, directly on the adhesive 12. The pheromone composition (any from Table 3, Example 4) 22 is applied directly to the non-adhered face of the handwarmer 20. A sealed plastic container 14 approximately 10 mm high and 70 mm diameter, with a 4 mm diameter hole 18 in the upper surface, is filled with a $CO_2$-generating formula 16, either CF1 or CF1S (Table 1, Example 1); the hole 18 allows $CO_2$ to escape from the plastic container 14.

FIG. 4 is a side view of the paper insect trap 10 of FIG. 3 device.

DETAILED DESCRIPTION OF THE INVENTION

Figure 1:
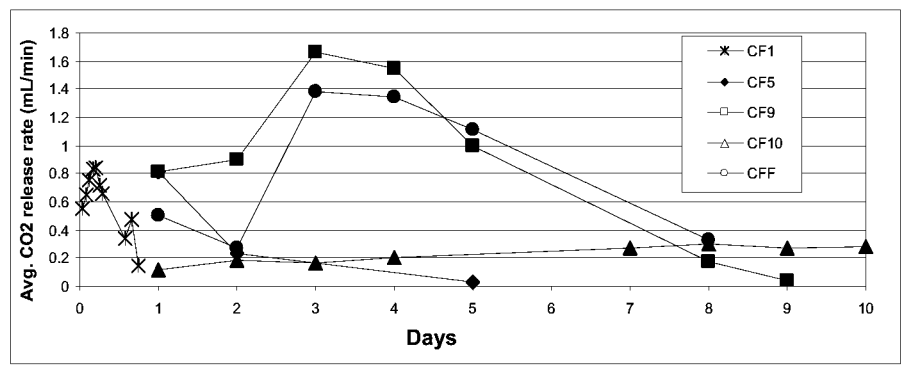
FIG. 1 graphically illustrates the release rates in mL/min of carbon dioxide ($CO_2$) from several $CO_2$-generating formulae (Table 1, Example 1).

The following description of the preferred embodiments of the invention is not intended to limit the invention to these preferred embodiments, but rather to enable any person skilled in the art to make and use this invention.

We have identified kairomone components, and kairomone formulations capable of attracting common and tropical bed bugs. Known mammalian pheromone compounds isolated from either porcine mammaries or boars were discovered to act as kairomones that attracted bed bugs. The compounds isolated from pregnant or suckling porcine mammaries consist of groups of fatty acids, which are also commonly found on human skin, and includes low-volatile components such as oleic acid, palmitic acid, linoleic acid, lauric acid, myristic acid, pentadecanoic acid, squalene, cholesterol, lauric acid, or 2,2-dimethyl 1,3-dioxolane-4-methanol. The boar-isolated pheromone androstenone (Lunde et al. *PLoS ONE*. 2012, 7(5):e35259) acted synergistically with the fatty acid compounds to attract bed bugs when combined with skatole (3-methyl indole, also isolated from boars and a known insect pheromone for mosquitoes and fruit flies).

The low-volatile kairomones were optimally released from an artificial device when heated in a manner that mimicked natural mammal exothermic skin conditions. Kairomones placed on a chemical heating pad that reached 100° F. or under a red light bulb that reached 140° F. increased attractancy of bed bugs.

Our experiments also showed that bed bugs are attracted to extremely low levels of carbon dioxide produced by microbial methods, that the microbial $CO_2$ could be produced from as little as 20 mL water for up to 30 hours, or for up to 14 days using 250 mL water. A synergistic attraction result occurred when bed bug attractants, especially skatole, were added to the $CO_2$ generator.

The optimal effect of attraction of bed bugs was discovered to occur from a combination of attractants, such as the kairomones of the instant invention, when vaporized from a heating source, which also attracts bed bugs, and a microbial $CO_2$ generator which also attracts bed bugs, and said microbial $CO_2$ generator including additional attractants.

As a result, the technologies combine to create both short-term, low cost and disposable devices, as well as long-term, economical devices that can efficiently attract bed bugs to a locus, such as a trap, bait station, counting station, detection apparatus or other such means to attract, monitor or trap bed bugs for surveying, monitoring, mitigation and management purposes.

EXAMPLES

Example 1

Sustained Release of Low Levels of Carbon Dioxide

Mixtures of white sugar (sucrose, CAS No. 57-50-1), dried baker's yeast (*Saccharomyces cerevisiae*), citric acid anhydrous (CAS No. 77-92-9), and warm tap water were combined as specified in Table 1. Fermentation of sugar by yeast into ethanol releases carbon dioxide ($CO_2$) as a by-product, among other gases. Citric acid lowered the initial pH of the solution to approximately pH 3, which slowed fermentation to a controlled rate. Carbon dioxide was presumed to be the main component of released gases.

TABLE 1

Combinations for producing very low rates of carbon dioxide via fermentation.

| Formula | Yeast (g) | Sugar (g) | Citric acid (g) | Water (mL) | Micro-cellulose (g) | Skatole (mg) |
|---|---|---|---|---|---|---|
| CF1 | 0.466 | 1.456 | 0.013 | 13 | 0.064 | 0.032 |
| CF1S | 0.466 | 1.456 | 0.013 | 13 | — | — |
| CF5 | 1 | 20 | 0 | 150 | — | — |
| CF9 | 2 | 40 | 0.4 | 400 | — | — |
| CF10 | 1 | 40 | 0.4 | 400 | — | — |
| CFF | 2 | 40 | 0.4 | 250 | — | — |

$CO_2$ production was measured with an apparatus whereby the gas released by fermentation displaced the water in a cylinder. Mixtures were combined in 250 mL Pyrex round media storage bottles (Sigma Aldrich #CLS 1295250) with vented polypropylene caps containing a single ⅛" through-hole fitted with an plastic port. A 5 mm diameter plastic hose was attached on one end to the port. The other end was inserted into a graduated 50 mL cylinder, which was then inverted in a 1 L container of water. The total amount of gas released was measured every 5 to 60 minutes (as necessary), and the release rate in milliliters per minute (mL/min) was determined by dividing the total gas released by the number of minutes elapsed since the previous measurement. Average $CO_2$ release rates per day for five carbon dioxide-producing compositions are illustrated in FIG. 1.

Flow rate of the CF1 formula was further tested as follows. Solid components were mixed with 15 mL water in plastic bottles with cone-shaped lids and swirled to mix. Tygon® tubing was attached to the top of the lid and the other end attached to glass tubing in a flow rate meter. Gas output was measured at 14, 16, 18, and 24 hours after mixing. The average of three replicates are indicated in Table 2.

TABLE 2

Flow rate measurements (avg. of 3 replications) in mL/min of $CO_2$ output.

| Formula | 14 hrs | 16 hrs | 18 hrs | 24 hrs |
|---|---|---|---|---|
| CF1 | 0.34 | 0.47 | 0.15 | 0 |

It was concluded that the CF1 formula released 0.5-0.8 mL/min $CO_2$ for at least 8 hours, and detectable amounts for up to 18 hours, making the composition suitable for short-term (single day), disposable devices. It was determined that CF5 released approximately 0.8 mL/min for the first day, CF9 and CFF released at least 0.4 and up to 1.6 mL/min for approximately 8 days, and CF10 released approximately 0.2 mL/min for at least 10 days. Any of CF9, CFF, and CF10 were deemed suitable for long-term (multi-day) devices. All release rates are considerably less than the published rates considered necessary to attract bed bugs (Singh et. al. 2012, Psyche (2012) Article ID 273613), although the lowest efficacious rate was noted by the authors as "exceed[ing] the bed bug response threshold", indicating that a rate lower than 200 mL/min could be efficacious. Unexpectedly, it was found that, even though formulas CF1 and CF10 produced levels as low as 0.5% of published $CO_2$ release rates, bed bugs were caught in traps baited with these formulae.

Example 2

Feasibility of Method and Two Trap Designs

Preliminary efficacy testing was performed at two locations with known bed bug infestations in the Seattle area. Location 1 was a homeless shelter which had not been treated for bed bugs, despite the severity of the infestation throughout the building. Location 2 was a homeless shelter which had recently been chemically treated for bed bugs.

Two trap styles were initially tested. The first trap (BT) was a 2-liter version of the trap of Banfield (U.S. Application 2009/1026257), which had been modified by gluing a light fabric 2.5 cm wide and 10 cm long from the base of the trap to the side entrance holes of the trap in order to allow bed bugs to ascent the slippery plastic trap walls. Attractant CF5 (Table 1, Example 1) was placed inside the trap to both attract bed bugs and to drown them in the liquid.

Figure 2:
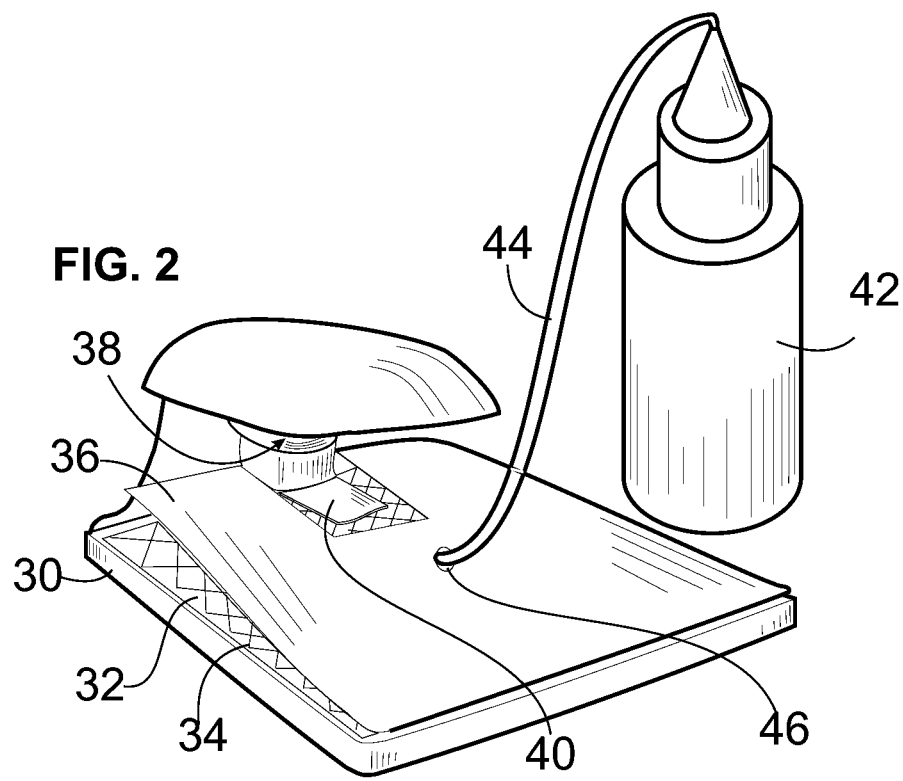
FIG. 2 schematically illustrates a trap (FT), suitable for short- or long-term use in the present invention, which is modified from the trap of Vaudry (U.S. Pat. No. 5,353,542) (Examples 2, 6-7, 11-12). The insect trap 30 is fitted with a sticky capture pad 32, which is covered with a plastic grid 34 with 12 mm spacing. The plastic grid 34 is covered with a 0.1 cm thick stiff, black plastic sheet 36, which rests against the trap 30, over the capture pad 32 area, at about a 5 degree angle. The plastic sheet 36 has a 0.635 cm hole 46 drilled through it to allow a 5 mm outer diameter plastic hose 44 to pass through it. The other end of the hose 44 is connected to a sealed bottle 42 which may contain any of the formulae from Table 1, Example 1. The red light bulb 38 provides attractive heat in addition to vaporizing the kairomone components from the kairomone pad 40. the kairomone pad 40 is placed on top of the plastic grid 34 and directly underneath the red light bulb 38 in order to release the kairomone components at a greater rate.

The second trap (FT) was a version of the trap of Vaudry (U.S. Pat. No. 5,353,542) 30 modified as illustrated in FIG. 2: (a) the electrical cord was removed and replaced with a 30 cm long, 5 mm diameter plastic hose 44. The other end of the hose was attached to a sealed bottle 42 containing CF5; (b) a hole large enough to allow the plastic hose to pass was drilled in the trap support pillar, allowing the hose to extend onto the insect capture area, and; (c) a plastic grid 34 with 12 mm spacing was placed on top of the capture pad 32 to serve to: (i) prevent the hose 44 from sticking to the capture pad 32, (ii) allow attractant $CO_2$ to disperse over the capture pad 32 and (iii) allow bed bugs to enter proximal to the attractant before they are captured to prevent the capture pad 32 from exceeding its capture capacity in areas distal from the attractant source and; (d) the trap FT was further modified by placing a 0.1 cm thick, stiff black polypropylene sheet 36 over the capture pad 32/screen 34 combination such that the distal edge fit into the distal edge of the insect capture pad area of the trap 30, and the proximal edge rested against the pillar of the trap, such that the sheet rested at about a 5 degree angle. This created a harborage for bed bugs of varying sizes to attract varying life stages of bed bugs.

One trap of each style (BT and FT), baited with CF5 were placed within five feet of each other under a bed in the sleeping areas at Location 1 and Location 2, where bed bugs had been reported recently by residents. A total of six rooms were treated between the two locations, three rooms at each location. Traps were checked at 24 hours after placement and retrieved at 48 hours.

No insects were caught in any of the traps at the Location 2 presumed due to the recent chemical treatments at that location. The location was not used for additional testing. At Location 1, no insects were caught in any of the BT traps, so those devices were not used for additional testing. One bed bug was caught in each of two of the FT devices; 67 bed bugs of all stages were caught in the third FT device.

It was concluded that the CF5 $CO_2$ mixture was effective at attracting bed bugs to an appropriately configured trap, even though the $CO_2$ release rate was 200-500× lower than release rates considered acceptable in the published literature (Example 1). The efficacy of very low release rates of $CO_2$ that are generated by micro-organisms solves the problem and expense of employing dry ice, pressurized $CO_2$ canisters, or acid-mineral-produced gas to attract bed bugs.

Example 3

Establishment of Baseline Catches in Un-Baited Sticky Traps

A third trap style (ST) was tested (SpringStar Inc., Woodinville, Wash.). ST was a simple, adhesive-coated paper 10 12.5 cm wide and 37.5 cm long, folded into a triangle shape such that the inner adhesive layer 12 was protected from dust and debris, but the sides were open to allow insects to enter and be trapped on the adhesive 12, as illustrated in FIG. 3 and FIG. 4. Two traps were placed on the floor, adjacent to the baseboards, approximately a meter apart in all four corners of a small (3 m×6 m) multi-purpose room at Location 1 (Example 1), for a total of 8 traps. Traps were retrieved after 24 hours and new traps were placed. This was repeated twice. An average of 1 bed bug was caught per trap. Another 8 traps were placed as previous and left for 7 days. After 7 days, there was an average of 6.75 bed bugs per trap, or 0.96 bed bugs per trap per day.

It was concluded that, contrary to published reports, bed bugs could consistently be caught on a simple sticky trap, even after the initial catches occurred, and that the first-caught insects did not repel later-caught insects.

Example 4

Comparison of Un-Baited Sticky Traps to Sticky Traps Baited with a Combination of Carbon Dioxide, Heat, and Pheromone Blend A pheromone blend which mimics mammalian skin secretions (especially porcine mammary skin secretions) was developed as taught by Pageat (U.S. Pat. No. 6,384,252). By "pheromone" it is meant a substance released by an individual of a particular species that acts as a chemical messenger to other members of the same species, said message acting to convey social, sexual, aggregative, alarm or other messages within the species. A mammalian pheromone combination can be comprised of: oleic acid, palmitic acid, linoleic acid, myristic acid, capric acid, and lauric acid. Androstenone is used as a pheromone in porcine mating. The compounds skatole, androstenone, and lactic acid were added in the ratios described in Table 3. Isopropanol and propylene glycol were used as solvents and adjuvants. For each formula, pheromone components were weighed into a container, adjuvants added, and gentle heating, stirring or shaking applied as necessary to solubilize all of the compounds.

TABLE 3

Pheromone lure combinations tested in trapping studies.

| Compounds | Concentration in test formula (w/w) | | | |
|---|---|---|---|---|
| | A1 | A2 | A3 | A4 |
| Pheromones | | | | |
| Skatole (3-methyl indole) | 0.0094% | 0.0094% | 0.0094% | — |
| Androstenone | 0.0110% | 0.0110% | 0.0110% | — |
| Oleic acid | 29.1253% | — | 25.0000% | 25.000% |
| Palmitic acid | 0.0094% | — | 8.0000% | 8.000% |
| Linoleic acid | 11.1416% | — | 10.0000% | 10.000% |
| Myristic acid | 8.9380% | — | 8.0000% | 8.000% |
| Capric acid | 0.3578% | — | 1.0000% | 1.000% |
| Lauric acid | 2.4026% | — | 10.0000% | 10.000% |
| Lactic acid | 8.1979% | — | 8.0000% | 8.000% |
| Adjuvants | | | | |
| Isopropanol | 23.8946% | 9.9796% | 19.9796% | 20.000% |
| Polypropylene glycol | 15.9122% | 90.0000% | 10.0000% | 10.000% |

Most of the pheromone components are non-volatile and have a very low vapor pressure; it was assumed that the pheromone would need to be heated in order to release attractive amounts of the compounds. A handwarmer (Hot Hands, Grabber Inc.) 20, which produces heat through iron oxidation reaction, was used as an insect attractant means, as taught by Townsend (U.S. Pat. No. 5,119,586). The handwarmer (HW) 20 was secured to the adhesive layer 12 on the upper inside face of the ST 10 from Example 3, and the pheromone mixture 22 A1 (Table 3) was applied directly to the other face of the handwarmer 20, as depicted in FIG. 3 and FIG. 4.

ST traps were baited with CF1+HW+A1 (0.15 mL pheromone blend A1, from Table 3) and then paired with un-baited ST traps in four corners of the room from Example 3. Attractant formula 16 CF1 (from Example 1) was placed in sealed plastic container 14 about the size of a hockey puck, approximately 10 mm high and 70 mm diameter, with a 4 mm diameter hole 18 in the upper surface to allow $CO_2$ to escape.

Figure 5:
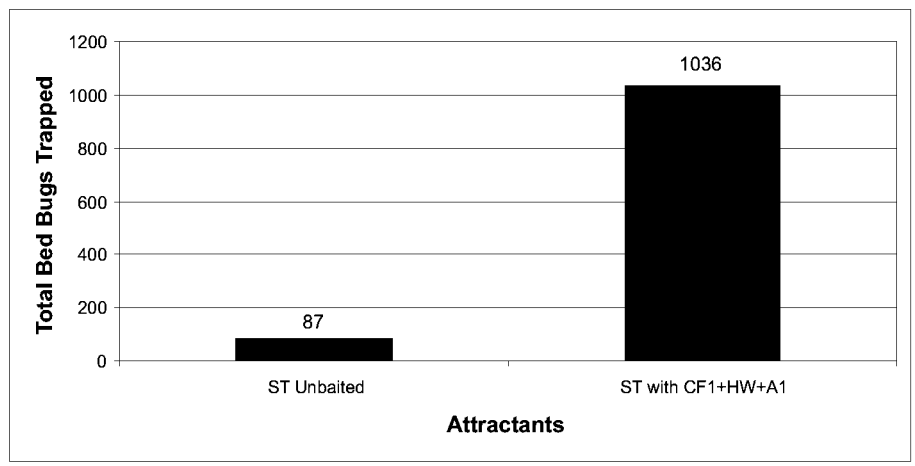
FIG. 5 graphically illustrates the total number of bed bugs caught in a sticky trap (ST) when using a combination of carbon dioxide (CF1) heat (HW) and a kairomone (A1) versus the total number of bed bugs caught in non-baited ST (Example 4).
Figure 6:
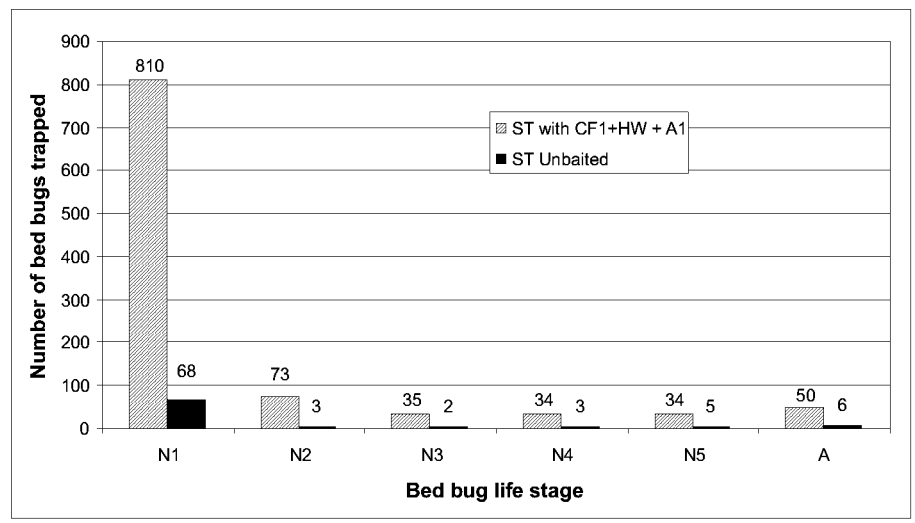
FIG. 6 graphically illustrates the total number of each bed bug feeding stage (N1-N5=$1^{st}$-$5^{th}$ instar nymph, A=adult) caught in a sticky trap (ST) when using a combination of carbon dioxide (CF1) heat (HW) and a kairomone (A1) to attract bed bugs, compared to the total number of each bed bug feeding stage caught in a non-baited ST (Example 4).

All traps were placed between 7 pm and 11 pm and retrieved at approximately the same time every day. New traps were used each day. This was repeated over seven days. To avoid positional influences, baited and unbaited traps were rotated between positions daily. All bed bugs trapped were counted and classified by feeding stage ($1^{st}$ instar nymph through adult) and, for adults, gender. Baited traps caught, on average, 11.9× more bed bugs per trap, as illustrated in FIG. 5. The proportion of each life stage trapped was not significantly different between the two treatments; baited traps caught more of all life stages than unbaited traps, as illustrated in FIG. 6.

It was concluded that the combination of CF1+HW+A1 effectively attracted 10 times more bed bugs than unbaited traps. Furthermore, unbaited traps placed within the same room as baited traps caught about 3 times more insects than unbaited traps placed in a room with no baited traps present (Example 3), suggesting that the attractants are disseminated beyond the traps they are released from. It was further concluded that the mammal pheromone compounds were employed by bed bugs as kairomones. By "kairomone" it is meant a substance released by an individual of a particular species that acts as a chemical messenger to other members of the same species, but the message is also intercepted and interpreted by a predating species as a signal to locate the first species as a host. As such, the pheromone blend will be referred to as a kairomone in following examples.

Example 5

Comparison to Another Style of Unbaited Sticky Trap

Figure 7:
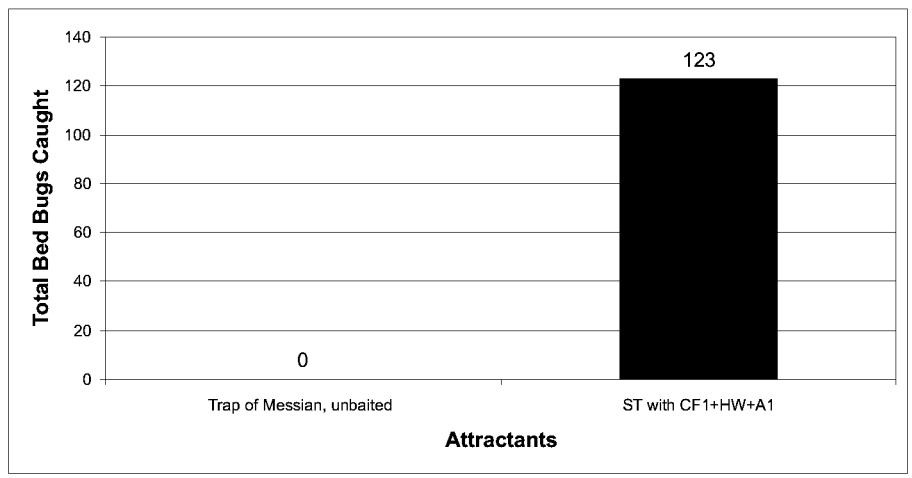
FIG. 7 graphically illustrates the total number of bed bugs caught in a ST trap baited with a combination of carbon dioxide (CF1) heat (HW) and a kairomone (A1), compared to the total number of bed bugs caught in the trap of Messian (U.S. patent application Ser. No. 12/998,399), which is not baited (Example 5).

ST traps baited with CF1+HW+A1 were paired with the trap of Messian (U.S. patent application Ser. No. 12/998,399, Atlantic Paste and Glue Inc., New York.) in three of the four corners of the room described previously in Example 3. Messian's traps were assembled and placed along the baseboards according to label directions. Trapped insects were counted and trap positions were swapped at 24 hours after placement. Traps were collected at 48 hours and trapped insects were counted. ST traps caught over 100 bed bugs, while in the same time period, the trap of Messian caught none, as illustrated in FIG. 7.

It was concluded that the ST traps baited with CF1+HW+A1 caught bed bugs, while the trap of Messian caught no bed bugs, even in a severely infested location. When compared with the results of Examples 3 and 4, it was concluded that the shape and style of sticky trap was an important component of the trap efficacy.

Example 6

Effect on Trap Catches of Adding Kairomone to Carbon Dioxide

Figure 8:
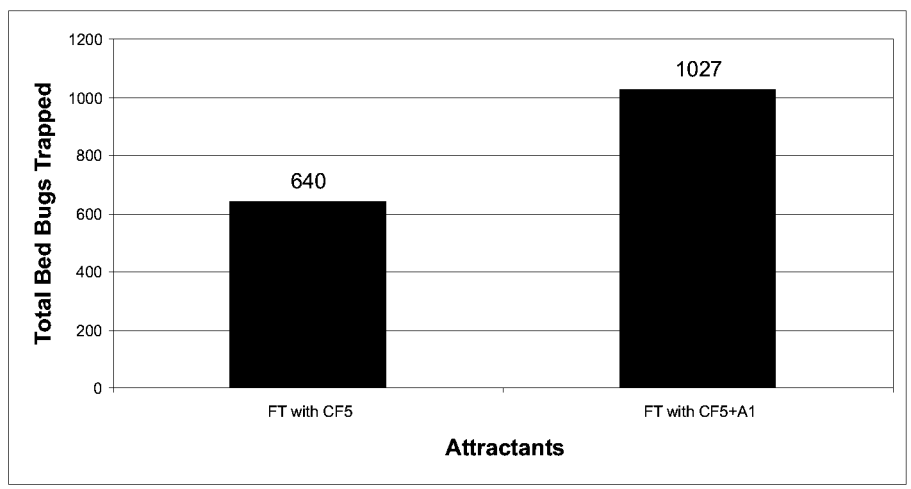
FIG. 8 graphically illustrates the total number of bed bugs caught in a modified trap of Vaudry (FT), when adding a kairomone (A1) to carbon dioxide (CF5) (Example 6).

FT traps, as in Example 2, baited with CF5+A1 were paired with FT traps baited with CF5 only. Kairomone A1 (0.25 mL)

was applied to a 0.635 cm×1.27 cm propylene felt pad 40, which was placed on top of the screen 34 near the outlet of the $CO_2$ tube 44. Pairs of traps were placed in three corners of the room described in Example 3, and positions were swapped daily to avoid positional effects. Traps were set up and retrieved the next day, as in Example 4. Traps baited with $CO_2$ and kairomone caught, on average, 1.6× more bed bugs per night, as illustrated in FIG. 8. One kairomone-baited trap caught 254 bed bugs in a single night; the maximum number caught by a $CO_2$-only trap was 112 bed bugs.

The kairomone also increased trap catches when combined with CF1. Solid components were mixed with 15 mL water in plastic bottles with cone-shaped lids and swirled to mix. Tygon® tubing was attached to the top of the lid, and the other end attached to a covered pitfall trap (The DOME Trap, Trécé Inc). Kairomone A1 (0.15 mL) was added to a 2.54 cm×2.54 cm compressed cardboard square, which was then placed in the center of the pitfall trap. Traps were baited with one of the following three combinations: CF1; A1; or CF1+A1. Traps were then placed in the center of a 60 cm×60 cm custom mock-bed arena in a laboratory (Location 3), 16 laboratory-reared bed bugs were released (8 adults and 8 late-stage nymphs), and total number of bed bugs caught were counted per day for 6 days. Four replicates per treatment were performed. The combined numbers are shown in Table 4. On average, CF1+A1 caught more bed bugs per replicate than the CF1 and A1 treatments combined.

TABLE 4

Bed bugs caught in covered pitfall traps baited with one of 3 attractant combinations.

| Attractants | # of Reps | No. of bed bugs caught | | | | | | Total | Avg |
|---|---|---|---|---|---|---|---|---|---|
| | | 1DAT | 2DAT | 3DAT | 4DAT | 5DAT | 6DAT | | |
| CF1 | 4 | 5 | 1 | 0 | 0 | 0 | 1 | 7 | 1.75 |
| CF1 + A1 | 4 | 10 | 2 | 0 | 0 | 0 | 0 | 12 | 3.00 |
| A1 | 4 | 1 | 0 | 1 | 0 | 0 | 0 | 2 | 0.50 |

It was concluded that adding kairomone to carbon dioxide treatments had a synergistic (i.e. more than additive) effect on bed bug trap catches.

Example 7

Effect on Trap Catches of Adding Heat to Kairomone and Carbon Dioxide

Figure 9:
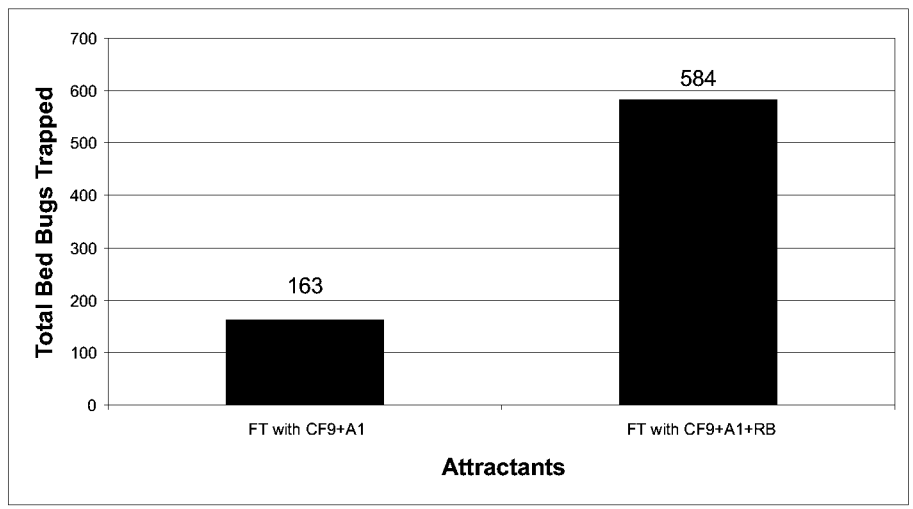
FIG. 9 graphically illustrates the total number of bed bugs caught in a FT trap when adding heat (red bulb, RB) to carbon dioxide (CF9) and a kairomone (A1) (Example 7).

Four FT (Example 2) were modified as follows: (a) the electrical cord was retained and the white light bulb was replaced with a red light bulb 38 to provide a heat and infrared source, as taught by Siljander et al. (U.S. Pat. No. 7,892,528); and (b) a 5 mm diameter plastic hose 44 was placed on top of the plastic grid 34 and the other end was attached to a sealed 400 mL bottle 42 containing CF9, as illustrated in FIG. 2. These modified FT traps were paired with the FT traps described in Example 2 and placed as in Example 3. Both types were baited with CF9+A1, as in Example 6. Traps with additional heat caught, on average, 3.6× more bed bugs that traps without, as illustrated in FIG. 9.

It was concluded that heat was an important attractive element, and that the combination of all three attractants was synergistic, i.e. more attractive than the individual elements alone, for trapping bed bugs in the FT trap.

Example 8

Effect on Trap Catches of Adding Kairomone to Carbon Dioxide and Heat

Figure 10:
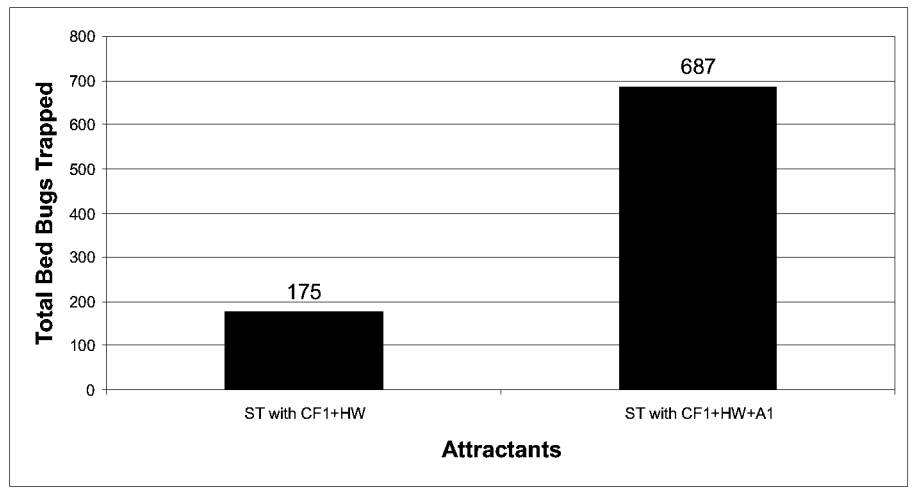
FIG. 10 graphically illustrates the total number of bed bugs caught when adding a kairomone (A1) to ST baited with carbon dioxide (CF1) and heat (HW) (Example 8).

ST baited with CF1+HW+A1 (as in Example 4) were paired with ST baited with CF1+HW, and placed as in Example 3 for six nights. Treatments were switched between positions daily, to prevent positional effects. Kairomone-baited traps caught, on average (±SE), 38.2±7.7 bed bugs per night; traps without caught 9.7±1.9 bed bugs per trap, as illustrated in FIG. 10.

It was concluded that the kairomone was an important attractive element, and that the combination of all three attractants was synergistic, i.e. more attractive than the individual elements alone, for trapping bed bugs in the ST trap.

Example 9

Effect on Trap Catches of Kairomone Components

The kairomone composition of A1 was split into it components by chemical class, to determine if all components were necessary. Three new kairomone blends were tested (Table 3, Example 4). Blend A2 contained only skatole and androstenone (male boar compounds), and the adjuvants. Blend A3 contained all the ingredients from A1, but in slightly different ratios. Blend A4 contained only the fatty acid components and adjuvants. Four treatments were tested as follows:

$$T0=CF1S+HW; T1=CF1+HW+A3; T2=CF1+HW+A2; T3=CF1+HW+A4$$

For treatment T0, the $CO_2$ blend was made without skatole (CF1S, Table 1, Example 1). All treatments were tested using ST traps assembled as in Example 4.

Figure 11:
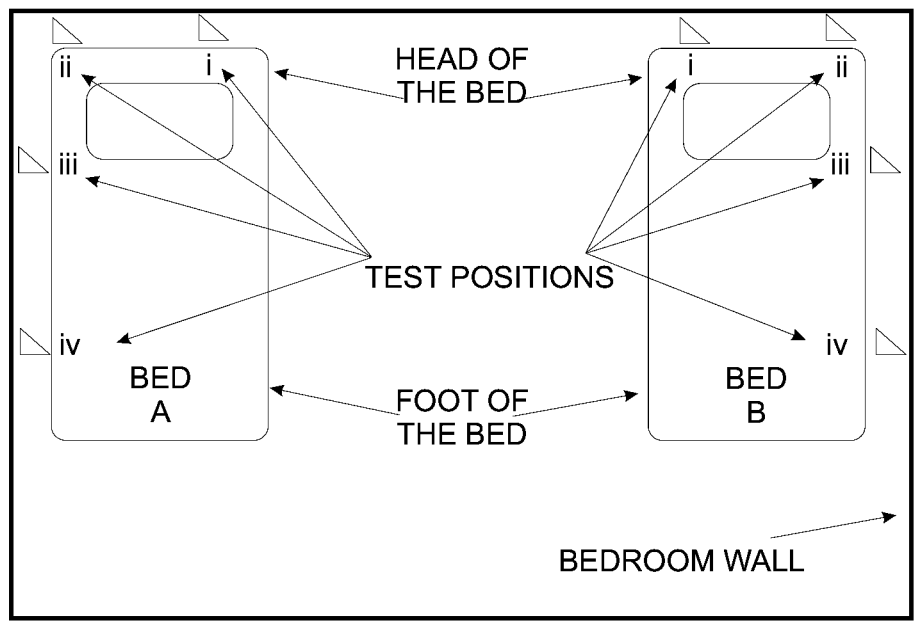
FIG. 11 schematically illustrates the layout of one of two bedrooms at Location 4, which were used for testing in Examples 9 and 11. The bedrooms were mirror images of each other. There were two beds in each room, indicated BED A and BED B. The bold outer line indicates the wall (including door and window) of each bedroom. Four TEST POSITIONS (indicated by triangles) were established on the floor around each bed as follows: i) at the HEAD OF THE BED, 30 cm from the outer edge (non-wall edge) of the bed; ii) in the corner of the room, behind the mattress; iii) at the inner edge (WALL edge) of the mattress, 30 cm from the corner of the room; and iv) between mattress and WALL, 30 cm from the FOOT OF THE BED.

A new location was used for testing kairomone components. Location 4 was an inhabited, 2-bedroom duplex in the suburbs of Seattle. Vacuum sampling estimated bed bug populations in each room at between 2,000 and 10,000 insects, which is considered heavily infested. Two people slept in the bedrooms on cots raised 50 cm off the carpet, which were then isolated from bed bugs in harborages by placing under each bed leg a plastic 16 oz drinking cup filled with propylene glycol or white pepper powder. Four test positions were established on the floor around each bed: i) at the head of the bed, 30 cm in from the outer edge of mattress; ii) in the corner of room, behind the mattress; iii) at the side of mattress, 30 cm from corner of room, and iv) between mattress and wall, 30 cm from foot of bed, as illustrated in FIG. 11.

Figure 12:
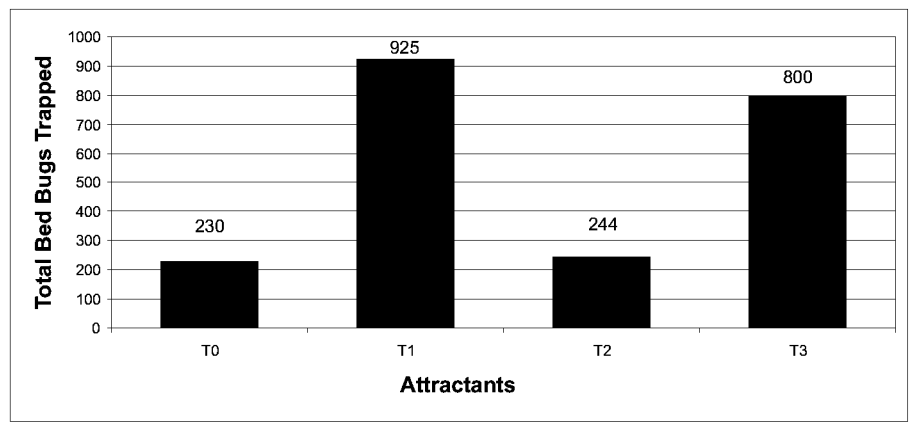
FIG. 12 graphically illustrates the total number of bed bugs caught in ST baited with one of four attractant combinations: T0) carbon dioxide (CF1S) and heat (HW); T1) carbon dioxide (CF1), heat (HW), and a combined attractant (A3); T2) carbon dioxide (CF1), heat (HW), and an attractant based off of male boar compounds (A2), or T3) carbon dioxide (CF1), heat (HW), and an fatty acid attractant (A4) (Example 9).

One treatment was placed per bed in each of the four test positions each night of the trial. Treatments were rotated between test positions in a crossover design to correct for positional effects. All traps were placed between 7 pm and 11 pm, and were retrieved the following day around the same time. New traps, which were newly baited, were used each day. This was repeated for eight days until all treatments had been tested in each test area twice. Results are summarized in FIG. 12.

It was determined that the full kairomone blend (A3) was more attractive than either of the component blends (A2 or A4), when combined with $CO_2$ and heat. It was noted that kairomone blend A2 was not significantly attractive by itself (T2; compare to no kairomone, T0); however, when added to the fatty acid component (A4), the resulting mixture (A3) was synergistically attractive (compare T1 vs T3).

Example 10

Effect on Trap Catches of Adding Skatole to Carbon Dioxide Bait

Four ST traps from Example 3, baited with CF1, were paired with four ST traps baited with CF1S. The skatole was incorporated into the fermentative mixture, in the ratios listed in Table 1, Example 1. Traps were placed in each of four corners of the location in Example 3. Traps were retrieved after one night. ST baited with CF1 caught, on average, almost twice as many bed bugs as traps baited with CF1S (3.75 bed bugs per CF1 trap vs 2.0 per CF1S). Additionally, all CF1 traps caught at least 2 bed bugs whereas half of the CF1S traps caught no bed bugs.

It was concluded that adding skatole to the fermentative mixture increased trap attractiveness to bed bugs. Both CF1 and CF1S caught more bed bugs than completely unbaited ST traps (Example 3).

Example 11

Feasibility of Trapping Method When Hosts are Present and Easily Accessible to Bed Bugs One FT baited with CF5 (as in Example 2), two ST baited with CF1+HW+A1 (as in Example 4), two ST baited with CF1 (as in Example 8) and one trap of Messian (as in Example 5) were placed in one bedroom (the "back bedroom") at Location 4 (from Example 9). An additional FT trap and one trap of Messian were placed in the other, less infested bedroom (the "front bedroom"). Two sleeping pads, which were regularly occupied at night by adult male humans, were placed directly on the floor in each bedroom. Traps were placed as follows:
1. FT+CF5: one trap at the foot of one sleeping pad in each bedroom
2. ST+CF1+HW+A1: one trap at the head of each sleeping pad or in the corner of the room adjacent to the pad, back bedroom only
3. ST+CF: one trap at the head of each sleeping pad or in the corner of the room adjacent to the pad; switched locations with ST+CF1+HW+A1 on alternate nights, back bedroom only
4. Messian: one trap against the wooden baseboard at the head of one sleeping pad in each bedroom ST traps were collected and the entire trap replaced after 24 and 48 hours. Only the removable capture pads from the FT traps were replaced at that time. After two days, the capture pads on the FT traps were replaced and left for an additional 13 or 14 days (back and front bedrooms, respectively) after which the entire trap was collected. One of the two traps of Messian was collected after 24 hours, the other was left for an additional 15 days and was collected with the final FT trap. Total number of bed bugs caught per trap type and per day are summarized in Table 5.

TABLE 5

Trap catch results. Unless specified, catches are combined for all traps of that type.

| Trap | Day 1 | Day 2 | Day 15 | Day 16 |
|---|---|---|---|---|
| ST + CF1 | 1 | 9 | — | — |
| ST + CF1 + HW + A1 | 4 | 1 | — | — |
| Trap of Messian | 0 (front) | — | — | 0 (back) |
| FT + CF5 | 0 | 0 | 47 (back) | 24 (front) |

It was concluded that the presence of human hosts negatively impacted catch rates of all devices and attractant blends when the hosts were readily accessible to the bed bugs. It was further concluded, comparing the results of Example 9 and Example 11, that the presence of hosts is only detrimental if the hosts are not isolated from the bed bugs. That is, bed bugs must not be able to easily reach their human hosts from their harborages in order for this method to be most efficacious.

Example 12

Ability of Method to Detect Bed Bugs in Very Low Level Infestations

An apartment building which had recently been heat-treated for a bed bug infestation was selected as a new test site (Location 5). Seven FT baited with CFF+RB+A1 were placed in three apartments. Traps were left in place for one week, after which the traps were collected and the sticky capture pads analyzed. An adult female bed bug was caught in one trap which had been placed underneath a sofa in the living room. That apartment was subsequently re-treated, after which no further bed bugs were found.

It was concluded that FT traps baited with all three tested attractants could detect low-level infestations, such as the few bed bugs left alive after a whole-building heat treatment.

Example 13

Ability of Device to Attract the Tropical Bed Bug, *Cimex hemipterus*

ST traps baited with CF1+HW+A1 were placed near known harborages in two locations in Singapore. The predominant bed bug in that country is *Cimex hemipterus*. Two sites were selected for field trials.

The first site (Location 6) was a 4-bedroom apartment, which had received chemical treatments for bed bugs. The chemical treatments had reduced but not eliminated the infestation. One trap was placed in the master bedroom, one in the common room, and one next to the sofa in the living room.

The second site (Location 7) was a dormitory room with eight double-decked beds, which had been treated multiple times for a persistent bed bug problem. Bed bugs were found to be harboring near power outlet boxes (suit boxes) and next to false ceiling boards, rather than in the bed frames, as can be typical in post-pesticide treatment scenarios. Eight traps were placed as follows: four in the corners above the false ceiling; two next to randomly selected bed frames; and two next to the suit boxes.

All traps were placed between 6:30 pm and 7:30 pm, near previously inspected harborages, and were collected after 24 hours. Results are summarized in Table 6.

TABLE 6

| | | Total | | |
|---|---|---|---|---|
| Site | Trap placement | caught | | Life stage(s) |
| Location 6 | master bedroom | 0 | — | |
| | common room | 4 | 3 | 1st instar |
| | | | 1 | 3rd instar |
| | living room (sofa) | 1 | 1 | 5th instar |
| Location 7 | suit boxes (1) | 8 | 2 1st instar | 4 3rd instar |
| | | | 1 5th instar | 1 adult male |
| | suit boxes (2) | 1 | 1 | adult male |
| | bed frame (1) | 1 | 1 | 2nd instar |
| | bed frame (2) | 0 | — | |
| | false ceiling (1) | 0 | — | |
| | false ceiling (2) | 0 | — | |
| | false ceiling (3) | 0 | — | |
| | false ceiling (4) | 0 | — | |

Tropical bed bugs trapped after 24 hours using ST baited with CF1 + HW + A1

It was concluded that the traps are attractive to the tropical bed bug. It was further noted that, despite large numbers of bed bugs being observed on the outside of the false ceiling, no bed bugs were caught in the traps placed above the false ceiling, as the bed bugs could not access the interior of the false ceiling, nor was the false ceiling on the path used by bed bugs when travelling from their harborage to host.

As a person skilled in the art will recognize from the previous detailed description and from the figures and claims, modifications and changes can be made to the preferred embodiments of the invention without departing from the scope of this invention defined in the following claims.

What is claimed is:

1. A method of attracting bed bugs, comprising dispersing at least one trap, the trap comprising:
   a) a bed bug attractant comprising: (i) at least one of oleic acid, palmitic acid, linoleic acid, lauric acid, capric acid, myristic acid, androstenone or 3-methyl indole, or derivatives thereof, or mammal pheromones; (ii) wherein said derivatives are esters, salts, alcohols, ketones, ethers or amides; and
   b) a carbon dioxide-generating means comprising: (i) brewers yeast: 0.20% to 0.75% by weight; and (ii) sugar: 9.00% to 14.00% by weight; and (iii) citric acid: 0.10 to 0.25% by weight; and (iv) water: 85.00% to 91.00% by weight; and
   c) a heating means in an area where bed bug populations are known or suspected to be present, or where attracting, monitoring, and/or trapping bed bug populations for surveying, monitoring, mitigation, and/or management purposes is desirable.

2. The method of claim 1, wherein said heating means is located sufficiently proximal to the bed bug attractant so as to increase volatility of said bed bug attractant.

3. The method of claim 1 wherein said carbon dioxide-generating means further comprises: 3-methyl indole, or its esters or salts or alcohols or ketones or ethers or amides, or the related compound 3-hydroxy-3-methyloxindole, 3-methyloxindole, 5-hydroxy-3-methylindole, 6-hydroxy-3-methylindole, or indole-3-carbinol, or derivatives thereof, wherein said derivatives are esters or salts or alcohols or ketones or ethers or amides.

* * * * *